United States Patent [19]

Tyszblat

[11] Patent Number: 5,447,967
[45] Date of Patent: Sep. 5, 1995

[54] COMPLETELY CERAMIC DENTAL PROSTHESIS BASED ON ALUMINA/MAGNESIA SPINEL AND A PROCESS FOR ITS MANUFACTURE

[76] Inventor: Michële Tyszblat, Courbevoie, France

[21] Appl. No.: 75,557

[22] Filed: Oct. 7, 1993

[30] Foreign Application Priority Data

Oct. 15, 1991 [FR] France ............... 9112673

[51] Int. Cl.$^6$ .............. A61K 6/08; C08K 3/18; A61C 13/00; B41C 3/08
[52] U.S. Cl. ................ 523/116; 523/109; 523/115; 524/433; 524/437; 524/441; 524/444; 433/171; 433/201.1; 433/202.1; 106/35; 501/32
[58] Field of Search .......... 523/116, 115, 109; 524/433, 437, 441, 444; 433/171, 201.1, 202.1; 264/17, 18; 106/35; 501/32

[56] References Cited

U.S. PATENT DOCUMENTS 4,954,080  9/1980  Kelly et al. .................. 433/8

FOREIGN PATENT DOCUMENTS 0030851  6/1981  European Pat. Off. .
0241384 10/1987  European Pat. Off. .
8808828 11/1988  WIPO .
8912436 12/1989  WIPO .

*Primary Examiner*—Paul R. Michl
*Assistant Examiner*—Lavonda DeWitt
*Attorney, Agent, or Firm*—Cushman Darby & Cushman

[57] ABSTRACT

The invention relates to a biocompatible ceramic dental prosthesis having a translucency similar to that of natural tooth enamel and a high mechanical strength.

It comprises a rigid, porous infrastructure obtained by the reactive calcination of fine particles of alumina/magnesia spinel, alumina and magnesia, the pores of which are occupied by glass infiltrated at high temperature.

The invention also relates to a manufacturing process for producing such a prosthesis.

20 Claims, No Drawings

COMPLETELY CERAMIC DENTAL PROSTHESIS BASED ON ALUMINA/MAGNESIA SPINEL AND A PROCESS FOR ITS MANUFACTURE

This invention relates to a translucid completely ceramic, dental prosthesis based on alumina/magnesia spinel and a process for its manufacture. A process for manufacturing dental prostheses is already known from the applicant's European Patent No 0 241 384, wherein such prostheses comprise a porous infrastructure obtained by the calcination of metal oxide particles, the pores of this infrastructure being ocuccupied by a glass which is infiltrated in the liquid state.

In addition, non-shrinking ceramic prosthetics are known from EP-A 0 030 851 containing aluminum oxide and magnesium oxide spinels but these also contain significant amounts of silicon oxide so that they lack translucency and therefore look very different from natural teeth.

This invention relates to translucid dental prostheses which are obtained by the infiltration of a glass into the pores of a solid infrastructure made from alumina/magnesia spinel which can be shaped either directly in the mouth by the dentist or on a model of the tooth by the prosthetist. The prostheses according to the invention have the advantages of being completely ceramic, of being translucent like natural tooth enamel, of being slightly colored or not coloured if this is desired, and of having a high mechanical strength, whilst being perfectly biocompatible. The dental prostheses according to the invention can advantageously but not in a limiting sense be used to produce the parts known by the names of "inlay" and "onlay" or for the production of crowns.

The object of this invention is a process for manufacturing translucid, ceramic dental prostheses like natural tooth enamel with increased mechanical resistance and being biocompabible, the process being characterized in that: a plastic paste is produced comprising a mixture of resin or organic binder with fine particles of alumina/magnesia spinel, alumina and magnesia; the said paste is given the shape which the prosthesis is to have; polymerization of the resin or setting of the binder is effected, in order to fix the shape of the paste; the paste thus formed is subjected to a thermal treatment, to effect firstly the calcination of the resin or of the resin binder, and secondly to effect the reactive calcination of the particles of alumina/magnesia spinel, alumina and magnesia; the porous infrastructure thus obtained may possibly be machined to shape; and this infrastructure is then infiltrated by means of a glass in the molten state.

It is known that spinels comprise complex cubic structures of metal oxides.

The spinel used according to the invention is the spinel formed from quantities of aluminum oxide or alumina ($Al_2O_3$) and magnesium oxide or magnesia (MgO) close to the stoichiometric composition.

In the description below, this spinel is designated by the term "$MgAl_2O_4$ spinel" or alumina/magnesia spinel.

It is known that this spinel is formed when a mixture of alumina and magnesia powders is placed in contact at high temperature.

The alumina and magnesia which, according to the invention, are added to the $MgAl_2O_4$ spinel combine at least partially during the reactive calcination to produce an additional quantity of $MgAl_2O_4$ spinel. This reaction leads to an increase in volume of the porous infrastructure which, depending on the thermal calcination treatment and the quantity of additional spinel formed, may comprise a variation in linear dimensions of between 0.6 and 4%.

This expansion enables an exact compensation to be effected for the contraction of the paste which occurs on the polymerization of the resin or on the setting of the binder, which for example may correspond to a reduction of 0.1 to 2% in the linear dimensions, as well as for the contraction due to the calcination of the resin or of the binder, which may correspond to a reduction of 0.5 to 2% in the linear dimensions.

In other words, according to the invention the mineral batch which is introduced into the paste to which the shape of the prosthesis is imparted comprises, besides spinel, additions of alumina and magnesia which expand on combining during the reactive calcination to compensate for the contraction which results from the polymerization of the resin or the setting of the binder after calcination.

According to the invention, the polymerizable resin usable in the paste is an organic resin which is destroyed on calcination, such as poly-epoxy, polyester or vinyl ester type resins.

The organic binder which can also be used in the paste may comprise a cellulose ester such as methyl cellulose, methyl hydroxyethyl cellulose, methyl hydroxypropyl cellulose, carboxymethyl cellulose or hydroxyethyl cellulose, or sodium or ammonium alginate, all of which are products which are soluble in water.

The organic binder may also comprise a cellulose ether such as ethyl cellulose or cellulose acetate, or polyvinyl butyral, which are soluble in organic solvents.

According to the invention, the resin or the binder, to the extent that this is possible, must not contain any compound such as silica which does not disappear on calcination. This is so because such compounds have the effect of causing the prosthesis to lose the translucency which characterizes the prostheses according to the invention.

According to a preferred method of carrying out the invention, the mineral batch used in the paste consists of a mixture of fine particles comprising 50 to 84 weight % of $MgAl_2O_4$ spinel, 10 to 32 weight % of alumina, and 6 to 18 weight % of magnesia.

These particles preferably have a particle size less than 40 microns, most preferably between 0.5 and 20 microns.

The polymerizable resin defined above in which the mineral batch (filler) can be incorporated comprises, for example, 40 to 90 weight % of poly-epoxy, polyester or vinyl ester resin, 0 to 80 weight % of a reactive monomer diluent, 0.5 to 5 weight % of catalyst, 0 to 4 weight % of accelerator and 0 to 10 weight % of plasticizer.

The organic binder defined above in which the mineral batch can be incorporated may comprise, for example, 3 to 15 weight % of organic binder, up to 10 weight % of plasticizer, and 75 to 95 weight % of water or organic solvent.

The paste to which the shape of the prosthesis is imparted advantageously contains 55 to 78 volume % of metal oxides, the remainder being composed of the resin or the binder defined above.

According to the invention, the paste thus obtained can be used directly by the dentist, who applies it to the previously prepared tooth which is to receive the prosthesis, and gives it the shape which the prosthesis must have. In this case, the binder sets in the mouth, whilst the resin undergoes photopolymerization in the mouth, followed by thermal polymerization after demoulding. In a variant, the resin is subjected to a chemical polymerization in the mouth, i.e. a polymerization via a chemical route.

It is also possible to impart the shape which the prosthesis is to have to the paste by applying the latter to a plaster model, followed by thermal polymerization of the resin or setting of the binder and then demoulding; this can be effected in a prosthesis laboratory.

If it is desired to form a prosthesis such as a crown in the mouth, it can be advantageous to use a porous ceramic shell which is easily machinable. Such a shell may comprise 70 to 100 weight % of $MgAl_2O_4$ spinel, up to 30 weight % of whiskers such as alumina, magnesia or mullite ($3Al_2O_3$-$2SiO_2$) whiskers, and up to 20 weight % of alumina or silica fibers. After being shaped by injection, this composition is subjected to calcination at 1200° to 1400° C. It then has an open porosity of 10 to 30 % by volume.

This shell will form the external surface of the prosthesis, which facilitates and greatly simplifies the shaping of the paste by the dentist to form the infrastructure.

When the paste is shaped in a laboratory, this is effected by taking the traditional impressions which are used for the manufacture of prostheses.

According to the invention, calcination of the blank thus obtained is carried out in a furnace in air, to effect firstly the calcination of the resin or the binder by raising the temperature to 400°–500° C. over 1 to 8 hours. According to the invention, this calcination reaction is carried out leaving a minimum of solid residue.

Secondly, the temperature is raised to about 1050°–1200° C. over 1 hour; it is then held constant for 1 to 4 hours, for example, to effect calcination (of the mineral batch).

After cooling, all that remains is a porous infrastructure which mainly comprises $MgAl_2O_4$ spinel; the alumina and magnesia which were present in the initial powder mixture have partially reacted with each other to produce additional spinel.

The infrastructure is then machined if it is necessary to change or adapt its shape.

Finally, the porous infrastructure is infiltrated by a glass provided in the liquid state at high temperature. For example, this infiltration is carried out by placing the porous infrastructure in a cupel on the powdered glass and raising the temperature to 600°–700° C. in air over 3 to 10 minutes, and then raising the temperature to 1100°–1200° C. under vacuum over 10 to 60 minutes, after which the temperature is held constant under vacuum for between 20 minutes and 2 hours, for example.

The glass may advantageously comprise a mixture of 12 to 30% of silica ($SiO_2$), 3 to 20% of alumina ($Al_2O_3$), 3 to 20% of boric oxide ($B_2O_3$), 15 to 45% of lanthanum oxide ($La_2O_3$), 0 to 15% of yttrium oxide ($Y_2O_3$), 0 to 8% of titanium dioxide ($TiO_2$), and 0 to 4% of coloring oxides.

If necessary, the excess glass is removed by sandblasting.

Finally, a bulk enamelling process is carried out, using a ceramic with a thermal expansion coefficient matched to that of the prosthesis thus obtained. In a variant, processing is restricted to polishing the prosthesis, which is itself translucent.

The present invention also concerns a biocompatible, ceramic dental prosthesis of similar translucency to teeth as well as having good mechanical resistance, characterized by the fact that it is obtained by the above described process and that it is made up of a rigid porous infrastructure obtained by reactive sintering (calcination) of fine particles of alumina/magnesia spinel, alumina and magnesia, the pores of said structure being filled by a glass introduced (infiltrated) subsequently at raised temperature.

For example, the overall composition by weight of the ceramic prosthesis according to the invention may be as follows:

| | |
|---|---|
| $MgAl_2O_4$ spinel | 45 to 70% |
| alumina | 8 to 20% |
| magnesia | 3 to 12% |
| glass | 20 to 40% |

The prosthesis of the invention may also advantageously be bulk enamelled using a ceramic whose coefficient of expansion is adapted to that of the prosthesis.

With the aim of providing a better understanding of the invention, several examples of fabrication will now be described, by way of illustration and without being limiting in any way.

Example 1

The following procedure is used to produce an inlay, to be formed in the mouth and intended to make good a loss of material which does not involve a cusp.

The dental cavity is first prepared, comprising cutting it away by drilling and imparting a suitable relief to it.

A paste is then prepared which has the following composition by weight:

| | |
|---|---|
| Metal oxide batch | |
| $MgAl_2O_4$ spinel | 70% |
| alumina | 19% |
| magnesia | 11% |
| Resin | |
| vinyl ester | 66.5% |
| reactive monomer diluent (triethylene glycol dimethacrylate) | 30% |
| catalyst (benzoyl peroxide) | 2% |
| photopolymerization activator (1,2-diketone benzyl camphroquinone) | 1.5% |

The paste is prepared by mixing 65 volumes of batch with 35 volumes of resin.

The paste thus obtained is placed in the mouth in such a way as to fill the cavity formed in the tooth, and the upper part of the paste is formed into the shape which the prosthesis must have.

Photopolymerization is effected by means of an ultraviolet lamp.

The prosthesis blank thus obtained is removed and thermally polymerized by heating it at 80° C. for 1 hour, followed by heating at 110° C. for 1 hour.

Calcination is then effected by bringing the blank to 100° C. over three hours which destroys the resin and then to 1120° C. over 1 hour; the latter temperature is maintained for 2 hours.

Infiltration of the glass is then effected, where the glass has the following composition by weight:

| | |
|---|---|
| $SiO_2$ | 20% |
| $Al_2O_3$ | 12% |
| $B_2O_3$ | 3% |
| $La_2O_3$ | 40% |

|  |  |
|---|---|
| TiO₂ | 7% |
| colouring oxides | 2% |

The prosthesis blank is placed in a cupel on the glass powder.

The temperature of the furnace is raised to 600° C. over 6 minutes, the furnace is evacuated and its temperature is raised to 1140° C. over 5 minutes; the furnace is maintained at 1140° C. for 30 minutes and is cooled in 10 minutes.

The prosthesis is then sandblasted to remove excess glass; it is then polished.

Finally, it is sealed or bonded in the mouth according to the usual technique.

Example 2

The following mode of operation is employed according to the invention to fabricate a crown which is shaped directly in the mouth by the dentist.

The dentist prepares the tooth by cutting it away and by drilling its perimeter to reduce its height and to produce a suitable relief.

He then selects a preformed dental shell which corresponds to the external shape which the crown is to have. Such shells are commercially available. They contain 80 weight % of $MgAl_2O_4$ spinel and 20 weight % of whiskers (mullite: $3Al_2O_3$-$2SiO_2$), for example.

The dentist places the shell in position by adapting its shape to the clinical case, either by drilling or by the addition of material by means of a polymerizable composite.

He prepares a paste which has the following composition by weight:

| Metal oxide batch | |
|---|---|
| $MgAl_2O_4$ spinel | 75% |
| alumina | 16% |
| magnesia | 9% |
| Resin | |
| A. Basic composition | |
| vinyl ester | 57% |
| reactive diluent | 40% |
| (diurethane-dimethacrylate monomer) | |
| accelerator | 3% |
| B. Catalyst | |
| vinyl ester | 57% |
| reactive diluent | 40% |
| (diurethane-dimethacrylate monomer) | |
| catalyst (benzoyl peroxide) | 3% |

The paste is prepared by mixing 62 volumes of batch with 38 volumes of resin before use (equal amounts of constituents A and B).

The dentist fills the shell with this paste and then places it in position on the tooth.

After chemical polymerization is completed, he removes it.

After finishing the edges, the prosthetist carries out a thermal treatment which comprises raising the temperature of the prosthesis blank to 400° C. over 6 hours to destroy the resin, then to 1160° C. over 1 hour 30 minutes. This temperature is maintained for 2 hours, after which the blank is allowed to cool.

He then proceeds to infiltrate the infrastructure, using a glass having the following composition by weight:

|  |  |
|---|---|
| $SiO_2$ | 20% |
| $Al_2O_3$ | 20% |
| $B_2O_3$ | 12% |
| $La_2O_3$ | 40% |
| $TiO_2$ | 8% |

The impregnation is effected as indicated previously by raising the temperature to 700° C. over 10 minutes in air, and then evacuating and raising the temperature to 1150° C. over 30 minutes and maintaining this temperature for 1 hour, after which the prosthesis is allowed to cool and then polished.

Example 3

The following procedure is employed to produce an onlay according to the invention, which is intended to make good a partial loss of material involving a cusp:

The dentist takes an impression of the tooth, reproduces its morphology using wax or resin, and produces a transparent cradle by thermal shaping; he then prepares the tooth by drilling and gives it a suitable relief.

He prepares a chemically polymerizable paste which has the following composition:

| Metal oxide batch | |
|---|---|
| $MgAl_2O_4$ spinel | 84% |
| alumina | 10% |
| magnesia | 6% |
| Resin | |
| A. Basic paste | |
| vinyl ester | 63% |
| diallyl phthalate | 32% |
| dimethyl para-toluidine | 3% |
| B. Catalyst | |
| vinyl ester | 65% |
| diallyl phthalate | 32% |
| benzoyl peroxide | 3% |

The paste is prepared before use by mixing 72 volumes of batch with 14 volumes of the basic paste A and 14 volumes of the catalyst B.

The dentist then places the cradle filled with paste in position on the tooth. When chemical polymerization is completed, he removes the prosthesis blank. The prosthetist then carries out a thermal treatment on the blank by heating it to 400° C. over 5 hours to destroy the resin and then to 1190° C. over 2 hours; the latter temperature is maintained for 2 hours. The blank is then allowed to cool naturally in the furnace.

The infrastructure is then impregnated with glass as indicated in the previous examples, where the glass used has the following composition by weight:

|  |  |
|---|---|
| $SiO_2$ | 15% |
| $Al_2O_3$ | 20% |
| $B_2O_3$ | 8% |
| $La_2O_3$ | 30% |
| $Y_2O_3$ | 15% |
| $TiO_2$ | 8% |
| coloring oxides | 4% |

Infiltration is effected by heating the blank to 700° C. over 6 minutes in air, then raising the temperature to 1180° C. over 20 minutes under vacuum, and cooling it in air to bring it back to ambient temperature in 10 minutes.

The excess glass is then removed and the blank is finished by polishing; the prosthesis is then fixed by bonding or sealing.

Example 4

The following procedure is used to produce an inlay on a previously prepared model of the tooth in the laboratory:

The dentist takes an impression of the prepared tooth, which is sent to the laboratory.

The prosthetist has to use a non-shrinkable plaster (less than 0.1%), which is heated to 100 to 120° C. over 2 hours.

He then makes a plaster model of the prepared tooth, and fills the undercuts with wax.

He applies a spacing varnish according to the traditional technique, and then a release agent comprising a non-reactive silicone oil, for example.

The prosthetist then fills the inlay cavity on the plaster model, using a paste which he prepares, and which has the following composition by weight:

| Metal oxide batch | |
|---|---|
| $MgAl_2O_4$ spinel | 50% |
| alumina | 32% |
| magnesia | 18% |
| Unsaturated polyester resin | |
| orthophthalic resin | 68% |
| copolymerizable monomer (diallyl phthalate) | 30% |
| catalyst (tertiary butyl ethyl-2 perhexanoate) | 2% |

The paste is obtained by mixing 55 volumes of batch with 45 volumes of resin before use.

The prosthetist applies the paste and sculpts it.

He then effects thermal polymerization by heating the prosthesis blank at 90° C. for 1 hour. He removes it after cooling., In order to achieve the reactive calcination of the infrastructure, its temperature is raised to 500° C. over 3 hours to destroy the resin, and then to 1180° C. over 1 hour; the latter temperature is maintained for 4 hours before allowing it to cool.

Infiltration is then carried out, using a glass having the following composition by weight:

| $SiO_2$ | 18% |
|---|---|
| $Al_2O_3$ | 10% |
| $B_2O_3$ | 18% |
| $La_2O_3$ | 30% |
| $Y_2O_3$ | 15% |
| $TiO_2$ | 8% |
| coloring oxides | 1% |

Infiltration is effected by heating the blank to 650° C. in air over 6 minutes, then raising the temperature to 1120° C. over 20 minutes under vacuum. The temperature is maintained at 1120° C. under vacuum for 25 minutes, then the prosthesis is cooled in 5 minutes.

The prosthetist then finishes the prosthesis by removing the excess glass and polishing it.

The prosthesis thus obtained is then fixed on to the tooth by bonding or sealing.

Example 4

The following procedure is used to produce a crown which is completely ceramic in the prosthesis laboratory.

The dentist prepares the tooth by giving it its size and relief, and takes an impression according to the conventional technique.

The prosthetist makes a plaster model of the tooth. He applies a spacing varnish to the model, followed by a release agent comprising a non-reactive silicone oil.

He then selects a preformed dental shell corresponding to the configuration of the crown, and machines it to adapt it to the patient's teeth by removing material by drilling, or by the addition of material.

He then fills the shell with a thermally polymerizable past9 having the following composition by weight:

| Metal oxide batch | |
|---|---|
| $MgAl_2O_4$ spinel | 80% |
| alumina | 13% |
| magnesia | 7% |
| Epoxy resin | |
| bisphenol A diglycidyl ether | 81.5% |
| reactive diluent (1-4 butane diol diglycidyl ether) | 15% |
| catalyst ($BF_3$:MEA: boron trifluoride - monoethylamine complex) | 3.5% |

The paste is prepared just before use, by mixing 66 volumes of batch with 34 volumes of resin.

After filling the shell with the paste, the prosthetist places it in position on the model, removes the excess paste, and finishes the edges, He then effects a thermal polymerization by heating it for one hour at a temperature of 130° C. After demoulding, he reheats it for 1 hour at a temperature of 180° C.

The prosthetist then heats the prosthesis blank to 500° C. over 8 hours to destroy the resin, then to 1170° C. over 1 hour, with the latter temperature being maintained for 2 hours. He then allows the prosthesis to cool in the furnace.

He then tests the infrastructure thus obtained by applying it to the model, and carries out any machining which may be necessary.

The infrastructure is then infiltrated according to the method described above with a glass having the following composition:

| $SiO_2$ | 20% |
|---|---|
| $Al_2O_3$ | 12% |
| $B_2O_3$ | 8% |
| $La_2O_3$ | 45% |
| $Y_2O_3$ | 5% |
| $TiO_2$ | 6% |
| coloring oxides | 4% |

Infiltration is effected by heating the blank to 600° C. in air over 10 minutes, then raising the temperature to 1150° C. over 40 minutes under vacuum. After maintaining the temperature at 1150° C. for 30 minutes under vacuum, the blank is allowed to cool.

The prosthetist then merely has to remove the excess glass, followed by polishing.

The crown can then be fixed in position by bonding or sealing.

Example 6

An inlay is produced according to the invention by proceeding as indicated in Example 4, using a paste having the following composition:

| Batch | |
|---|---|
| MgAl$_2$O$_4$ spinel | 84% |
| alumina | 10% |
| magnesia | 6% |
| Resin | |
| vinyl ester | 50% |
| monomer diluent (triethylene glycol dimethacrylate) | 48% |
| catalyst (benzoyl peroxide) | 2% |

The paste is obtained by mixing 75 volumes of batch with 25 volumes of resin.

Thermal polymerization is effected on the model of the tooth in an oven for 1 hour at 80° C., then for 1 hour at 120° C. After cooling and demoulding, calcination is effected by raising the temperature to 400° C. over 3 hours to destroy the resin then raising it to 1060° C. over 1 hour. This temperature of 1060° C. is then maintained for 4 hours, followed by allowing the blank to cool.

The prosthetist then checks the infrastructure and machines it if necessary.

He then effects infiltration with a glass with the following composition by weight:

| SiO$_2$ | 20% |
|---|---|
| Al$_2$O$_3$ | 9% |
| B$_2$O$_3$ | 18% |
| La$_2$O$_3$ | 45% |
| TiO$_2$ | 4% |
| coloring oxides | 4% |

The thermal infiltration cycle consists of raising the temperature to 700° C. over 3 minutes in the presence of air, then raising the temperature to 1100° C. over 15 minutes under vacuum. The temperature is held at 1100° C. for 12 minutes under vacuum, then the prosthesis is cooled in air in 8 minutes.

The prosthetist removes the excess glass by sandblasting.

He then carries out a bulk enamelling of the prosthesis, using classical dental ceramic, the coefficient of expansion of which matches that of the infrastructure. For example, a ceramic with the following composition by weight can be used:

| sodium oxide (Na$_2$O) | 4.7 to 4.2% |
|---|---|
| potassium oxide (K$_2$O) | 8.2 to 6.8% |
| calcium oxide (CaO) | 1.8 to 1.5% |
| aluminum oxide (Al$_2$O$_3$) | 13 to 15% |
| silica (SiO$_2$) | 62.8 to 68% |
| boric oxide (B$_2$O$_3$) | 7.5 to 8.5% |

The prosthesis is then fixed on to the tooth by sealing or bonding.

Example 7

An onlay prosthesis is produced according to the invention by the procedure as indicated in Example 4, using a paste with the following composition by weight:

| Batch | |
|---|---|
| MgAl$_2$O$_4$ spinel | 70% |
| alumina | 20% |
| magnesia | 10% |
| Resin | |
| vinyl ester | 60% |
| styrene | 38% |
| catalyst (tert-butyl perbenzoate) | 1.8% |
| accelerator (dimethylaniline) | 0.2% |

The paste is prepared before use by mixing 65 volumes of batch with 35 volumes of resin.

Thermal polymerization of the infrastructure on the model of the tooth is effected in an oven for 1 hour at 100° C., and then for 1 hour at 120° C.

After demoulding, calcination is effected by raising the temperature to 460° C. over 4 hours to destroy the resin and then to 1120° C. over 1 hour. The temperature of 1120° C. is held for 2 hours, after which the blank is allowed to cool.

The infrastructure is machined if necessary, and then infiltrated as indicated previously with a glass having the following composition by weight:

| SiO$_2$ | 80% |
|---|---|
| Al$_2$O$_3$ | 6% |
| B$_2$O$_3$ | 20% |
| La$_2$O$_3$ | 25% |
| Y$_2$O$_3$ | 15% |
| TiO$_2$ | 4% | using a thermal cycle consisting of raising the temperature to 600° C. over 6 minutes in the presence of air, and then raising the temperature to 1140° C. over 20 minutes under vacuum. The temperature of 1140° C. is held for 20 minutes under vacuum, followed by cooling in air over 10 minutes.

The excess glass is then removed by sandblasting, and a bulk enamelling is effected using a dental ceramic having a coefficient of expansion compatible with that of the prosthesis.

A ceramic having the following composition can be used for this purpose:

| sodium oxide | 4.5% |
|---|---|
| potassium oxide | 7.5% |
| calcium oxide | 1.7% |
| aluminum oxide | 14% |
| silica | 65.3% |
| boric oxide | 7% |

Finally, the onlay is fixed in position by sealing or bonding.

Example 8

The procedure for producing an inlay according to the invention in the laboratory is as indicated in Example 4, using a paste consisting of:

| Metal oxide batch | |
|---|---|
| MgAl$_2$O$_4$ spinel | 84% |
| alumina | 10% |
| magnesia | 6% |
| Liquid | |
| H$_2$O | 88% |
| organic binder (methyl cellulose) | 7% |

-continued

| plasticizer (polyethylene glycol 400) | 5% |
|---|---|

The above compositions are given in weight percent.

The paste is prepared at the time of use by mixing 70 volumes of batch with 30 volumes of liquid.

The inlay is modelled, and then dried for 1 hour in an oven at 80° C.

After demoulding, the infrastructure is calcined by heating it to 500° C. over 1 hour to destroy the binder and then to 1130° C. over 1 hour, with the latter temperature being maintained for 2 hours.

After cooling, machining of the infrastructure is carried out if necessary. The infrastructure is then treated as indicated in Example 4.

Example 9

The procedure for producing an inlay according to the invention is as indicated in Example 4, using a paste comprising:

| Metal oxide batch | |
|---|---|
| MgAl$_2$O$_4$ spinel | 73% |
| alumina | 18% |
| magnesia | 9% |
| Liquid | |
| H$_2$O | 85% |
| binder (methyl hydroxypropyl cellulose) | 15% |

The compositions given above are in weight percent.

The paste is prepared just before use by mixing 63 volumes of the metal oxide batch with 37 volumes of liquid.

In a variant, the liquid may comprise:

| solvent (2/3 trichloroethylene-1/3 ethanol) | 85% |
|---|---|
| binder (ethyl cellulose) | 15% |

The blank formed using this paste is dried for 1 hour in an oven at 80° C., followed by demoulding.

It is then calcined by being heated to 500° C. over 2 hours, to destroy the binder and then to 1150° C. over 1 hour, with the latter temperature being maintained for 2 hours.

After cooling, the procedure is as indicated in Example 6.

Example 10

The procedure for producing an onlay according to the invention is as indicated in Example 4, using a paste comprising:

| Metal oxide batch | |
|---|---|
| MgAl$_2$O$_4$ spinel | 78% |
| alumina | 14% |
| magnesia | 8% |
| Liquid | |
| H$_2$O | 87% |
| binder (ammonium alginate) | 3% |
| Plasticizer (polypropylene glycol) | 10% |

The percentages given above are by weight.

The paste is prepared at the time of use by mixing 65 volumes of batch with 35 volumes of liquid.

In a variant, the liquid may comprise:

| Plasticizer (octyl phthalate) | 10% |
|---|---|
| organic solvent (a mixture of 63% trichloroethylene and 24% ethanol) | 87% |
| binder (polyvinyl butyral) | 3% |

After modelling the inlay, it is dried for 30 minutes at 80° C. in an oven.

After demoulding, calcination is effected by heating the blank to 450° C. over 1 hour 30 minutes, and then to 1150° C. over 1 hour, with the latter temperature being maintained for 2 hours.

After cooling, the procedure is as indicated in Example 7.

In all the practical examples described above, biocompatible ceramic prostheses of translucency similar to that of teeth and having a good mechanical solidity, have been obtained.

I claim:

1. A process for manufacturing translucent ceramic dental prosthesis, having a heightened mechanical resistance and being biocompatible, said process comprising the steps of producing a plastic paste which is a mixture of a binder with fine particles of alumina/magnesia spinel, alumina and magnesia; said binder being an organic binder; imparting to said paste the shape which is necessary for the creation of the prosthesis; setting said binder in order to fix the shape of the paste; subjecting the paste thus shaped to a thermal treatment to effect calcination of said binder and to sinter said particles of alumina/magnesia spinel, alumina and magnesia so as to obtain a porous infrastructure; impregnating said infrastructure with a glass in the molten state and cooling the structure to ambient temperature.

2. The process according to claim 1, in which the quantities of alumina and magnesia present are such that under the sintering conditions they give rise to the formation of an additional quantity of alumina/magnesia spinel such that it induces an expansion of the infrastructure which compensates for the contraction of the prosthesis resulting from the calcination and from the sintering of the infrastructure.

3. The process according to claim 1, in which said binder is a polymerizable organic resin.

4. The process according to claim 3, in which the polymerizable organic resin is selected from the group consisting of poly-epoxy, polyester or vinyl ester resin.

5. The process according to claim 3, in which the shape fixation of the paste is caused by photopolymerization, chemical polymerization or thermal polymerization of the resin.

6. The process according to claim 1, in which said organic binder is a cellulosic compound selected from the group consisting of methyl cellulose, methyl hydroxyethyl cellulose, methyl hydroxylpropyl cellulose, carboxymethyl cellulose, ethyl cellulose and cellulose acetate.

7. The process according to claim 1, in which said organic binder is a sodium or ammonium alginate.

8. The process according to claim 1, in which said organic binder is a polyvinyl butyral.

9. The process according to claim 1, in which said paste comprises 50 to 84 weight percent of alumina/magnesia spinel particles, 10 to 32 weight percent of alumina particles, and 6 to 18 weight percent of magnesia particles.

10. The process according to claim 4, in which said polymerizable resin comprises 40 to 90 weight percent of a polyepoxy, polyester or vinyl ester resin, 0 to 80 weight percent of a reactive monomer diluent, 0.5 to 5 weight percent of a catalyst, 0 to 4 weight percent of an accelerator, and 0 to 10 weight percent of a plasticizer.

11. The process according to claim 1, in which the size of said particles of alumina/magnesia spinel, alumina and magnesia is less than 40 microns.

12. The process according to claim 1 wherein the size of said particles of alumina/magnesia spinel, alumina and magnesia is between 0.5 micron and 20 microns.

13. The process according to claim 1, in which said paste comprises 55 to 78 percent by volume of fine particles of alumina/magnesia spinel, alumina and magnesia.

14. The process according to claim 1, comprising the step of forming the plastic paste by applying the same in the mouth to a previously prepared tooth.

15. The process according to claim 1, comprising the step of forming the plastic paste by applying it to a plaster model.

16. The process according to claim 1, comprising the step of using a porous, machinable, ceramic shell for imparting to the plastic paste the external shape which the prosthesis is to have.

17. The process according to claim 1, in which the porous infrastructure is machined to the given shape before being impregnated.

18. A biocompatible translucent ceramic dental prosthesis having a high mechanical strength, obtained by the process of claim 1, said dental prosthesis comprising a rigid porous infrastructure of sintered powder made essentially of alumina/magnesia spinel, alumina and magnesia, the pores of said structure being occupied by a continuous mass of glass.

19. A prosthesis according to claim 18, which comprises essentially 45 to 70 weight percent of alumina/magnesia spinel, 8 to 20 weight percent of alumina, 3 to 12 weight percent of magnesia and 20 to 40 weight percent of glass.

20. A prosthesis according to claim 18, comprising a coverage of a ceramic enamel having a coefficient of expansion which is substantially the same as that of the prosthesis without enamel.

* * * * *

UNITED STATES PATENT AND TRADEMARK OFFICE
CERTIFICATE OF CORRECTION

PATENT NO.    :    5,447,967
DATED         :    September 5, 1995
INVENTOR(S)   :    TYSZBLAT It is certified that error appears in the above-identified patent and that said Letters Patent is hereby corrected as shown below:

On the Title page:

Delete

"[22]   Filed:    Oct. 7, 1993"

and insert

--[22] PCT Filed: Oct. 15, 1992

[86] PCT No.:  PCT/FR92/00974

§ 371 Date:  Oct. 7, 1993

§ 102(e) Date:  Oct. 7, 1993--.

Signed and Sealed this

Eleventh Day of June, 1996

Attest:

BRUCE LEHMAN

Attesting Officer    Commissioner of Patents and Trademarks